United States Patent [19]
Mejslov

[11] Patent Number: 6,086,575
[45] Date of Patent: Jul. 11, 2000

[54] SUBCUTANEOUS INFUSION DEVICE

[75] Inventor: Jesper Mejslov, Roskilde, Denmark

[73] Assignee: Maersk Medical A/S, Lynge, Denmark

[21] Appl. No.: 09/045,448

[22] Filed: Mar. 20, 1998

[51] Int. Cl.[7] .................................................. A61M 25/16
[52] U.S. Cl. ............................ 604/533; 604/93; 604/905; 604/535
[58] Field of Search .............................. 604/93, 174, 177, 604/175, 890.1, 242, 243, 167, 905, 256, 533, 534, 535, 537, 538

[56] References Cited

U.S. PATENT DOCUMENTS

| | | |
|---|---|---|
| 4,578,063 | 3/1986 | Inman et al. .............................. 604/175 |
| 5,522,803 | 6/1996 | Teissen-Simony . |
| 5,545,143 | 8/1996 | Fischell . |
| 5,980,506 | 11/1999 | Mathiasen ................................ 604/533 |

Primary Examiner—Corrine McDermott
Assistant Examiner—Cris L. Rodriguez
Attorney, Agent, or Firm—Brinks Hofer Gilson & Lione

[57] ABSTRACT

The invention relates to a subcutaneous infusion device comprising a housing; a flow channel within the housing; a cannula extending from the housing and being in flow communication with the flow channel; a connector for delivery of fluid into the flow channel; guide means for guiding the connector into a delivery position; the guide means being being arranged axis-symmetrically in relation to the axis needle along which the needle extends. By providing the guide means in such a manner there is no longer a need for an angular positioning of the connector in relation to the housing since guiding function is provided in any angular position of the connector in relation to the housing.

10 Claims, 4 Drawing Sheets

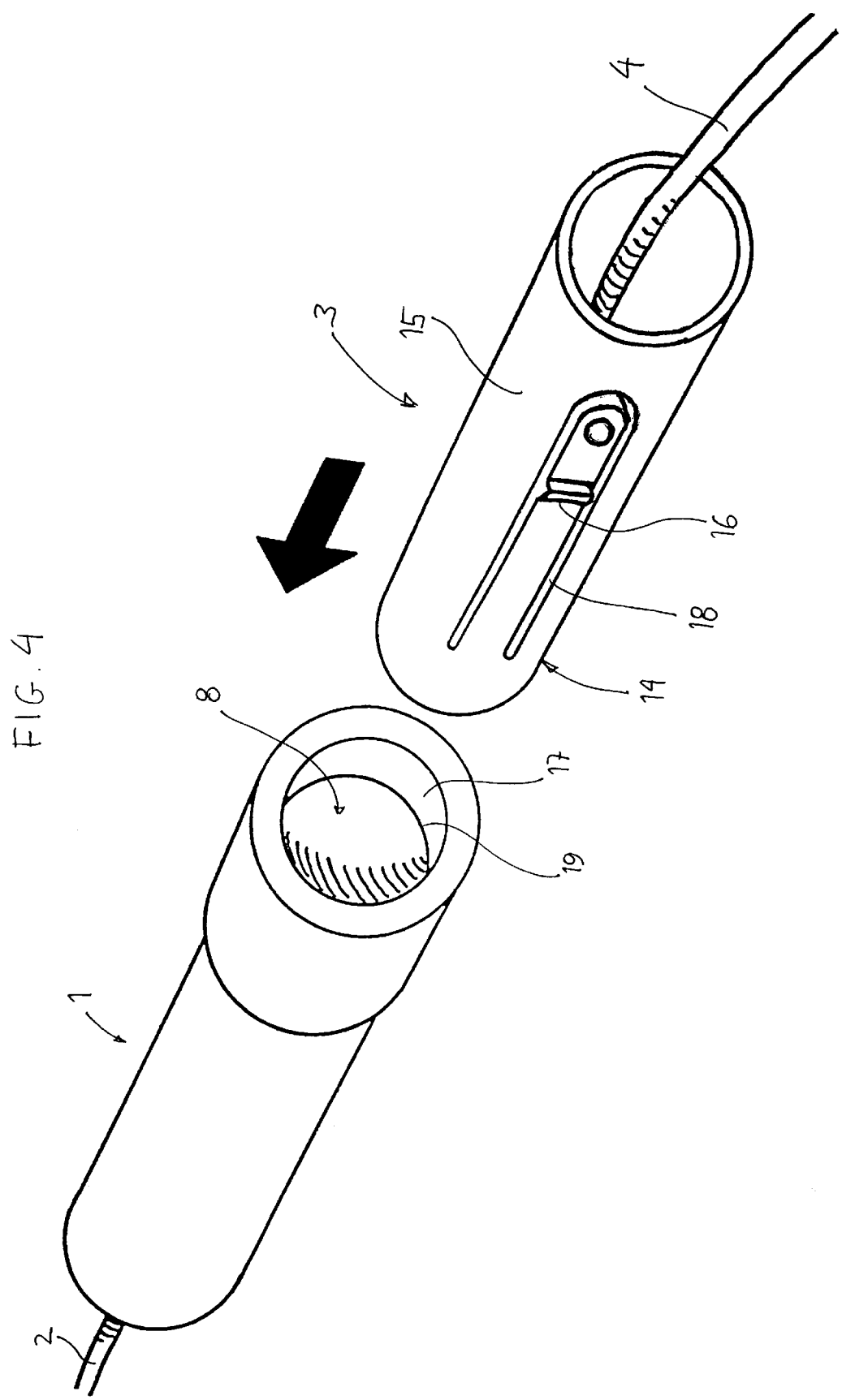

SUBCUTANEOUS INFUSION DEVICE

BACKGROUND OF THE INVENTION

The present invention relates to infusion devices for subcutaneous delivery of a medication or a therapeutic fluid by means of an external infusion system and more particularly to an infusion device having releasably connected means for delivery of the medication or the therapeutic fluid from the external infusion system.

Infusion devices are generally known in the art for delivering a medication or a therapeutic fluid to a subcutaneous site in a patient. Such devices commonly comprise a tubular cannula extending from a housing adapted to receive the desired medication via disconnectable means for suitable connection to further components of the infusion system. The possibility of disconnecting the infusion set from the further parts of the infusion system is provided in order to improve the user comfort. The user is enabled to perform activities which do not allow the presence of a pump or the like, or which are hindered by the presence of a pump or the like. In the disconnected state only a part of the infusion set is worn by the patient. This allows for increased mobility. In order to provide such disconnectable means and still maintain a fluid-tight sealing towards the interior of the housing and the tubular cannula that prevents contamination of the injection site, such devices are commonly provided with a self-sealing penetrable septum on either the housing or the disconnectable part and a hollow needle on the other part adapted to penetrate the septum. Upon withdrawal of the needle from the septum this provides a fluid-tight sealing towards the interior of the housing. The septum and the needle further provides a fluid-tight sealing between the housing and the connector means when medication or therapeutic fluid is delivered to the patient from the external infusion system. Subcutaneous infusion devices of this generally known type are known from e.g. U.S. Pat. No. 5,522,803 to Teissen-Simony and U.S. Pat. No. 5,545,143 to Fischell.

The assembly of the housing and the connector is rather cumbersome in connection with these prior art infusion devices. This is caused by the need of positioning the connector correct in both the axial direction and the angular direction in relation to the housing before a correct assembly can be realised.

Further devices of the disconnectable type are known, e.g. from U.S. Pat. No. 4,966,588. These earlier known devices do however not comprise guide means and therefor these devices can be difficult to handle for the user during the insertion of the connector needle into the housing.

For these reasons there is a need for improvements in the infusion devices of the type mentioned in the foregoing, and particularly with respect to providing an infusion device which is far less cumbersome from a user point of view and by means of which it is much easier to connect the connector and the housing. The infusion device according to the invention remedies the above mentioned disadvantages and provides further advantages which will become apparent from the following description.

SUMMARY OF THE INVENTION

According to the invention a subcutaneous infusion set has been developed wherein said subcutaneous infusion set comprises:
a housing;
a flow channel within the housing;
a cannula extending from the housing and being in flow communication with the flow channel;
a connector for delivery of fluid into the flow channel;
guide means for guiding the connector into a delivery position;
the guide means being arranged axis-symmetrically in relation to the axis of the connector.

By providing the guide means in such a manner there is no longer a need for an angular positioning of the connector in relation to the housing since guiding function is provided in any angular position of the connector in relation to the housing.

In a preferred embodiment the subcutaneous infusion device comprises a self sealing septum covering the flow channel and a needle on the connector for penetrating the self-sealing septum covering the flow channel, said needle extending along an axis. This embodiment ensures a proper sealing of the flow channel and a proper delivery through the septum. The guide means are in this connection arranged axis-symmetrically in relation to the needle axis.

The guide means conveniently comprises a cavity in the housing, the cavity having a circular inner wall and the connector has an outer wall mating with the inner wall of the cavity in the housing in a rotatable but not transversely dislocatably manner upon insertion of the connector. In this connection the outer wall of the connector mating with the cavity of the housing preferably has an outer circular cross-section.

In a slightly different embodiment the guide means comprises a cavity in the connector, the cavity has a circular inner wall and the housing has an outer wall mating with the inner wall of the cavity in the connector in a rotatable but not transversely dislocatably manner upon mounting of the connector. In this connection the outer wall of the housing mating with the cavity of the connector has an outer circular cross-section.

Advantageously means for interlocking the housing and the connector are provided. Such means are preferably arranged with an ability of interlocking in any angular position of the connector in relation to the housing.

In a preferred embodiment the locking means form part of the connector wall mating with the wall of the cavity of the housing. In one preferred embodiment the connector wall is of a tubular configuration and where two incissions parallel to the needle axis provide a flexible locking arm having a protrusion and the cavity in the housing comprising a circumferential groove arranged to angage with the protrusion of the locking arm.

In anothet preferred embodiment the locking means form part of the wall of the housing mating with the wall of the cavity of the connector. In one preferred embodiment the wall of the housing is of a tubular configuration and where two incissions parallel to the needle axis provide a flexible locking arm having a protrusion and the cavity in the connector comprising a circumferential groove arranged to angage with the protrusion of the locking arm.

BRIEF DESCRIPTION OF THE DRAWINGS

FIG. 4 is a side view of the connector forming part of the infusion device shown in FIG. 1;

DESCRIPTION OF THE PREFERRED EMBODIMENTS

Figure 1:
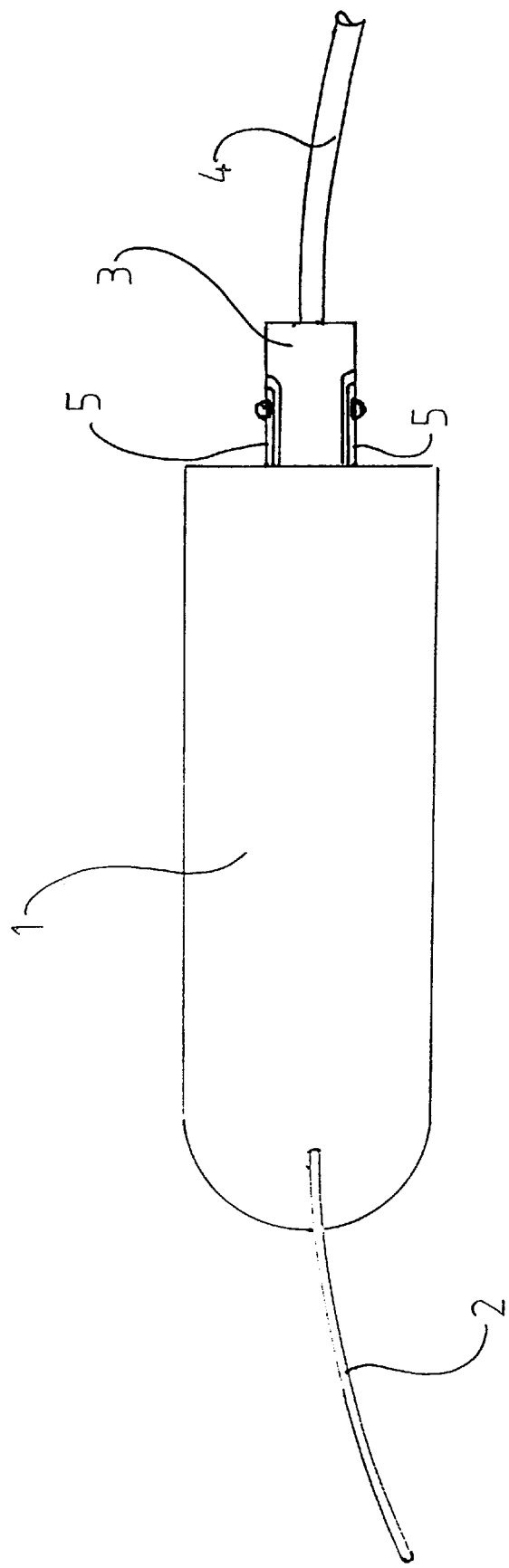
FIG. 1 is a top view of a subcutaneous infusion device according to the invention.

It appears from FIG. 1 that the preferred embodiment of the infusion device comprises a housing 1 and a soft cannula 2 extending from the housing. A connector 3 is connected to the housing and a hose 4 extends from the connector for providing fluid communication between a pump (not shown) and the connector.

Figure 2:
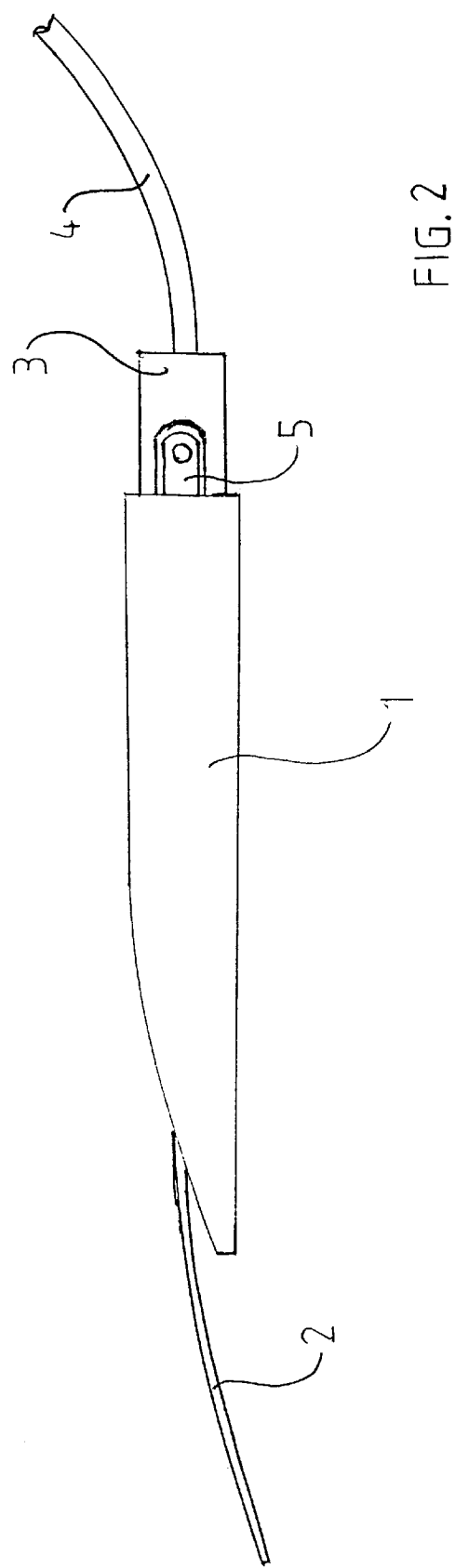
FIG. 2 is a side wiev of the device shown in FIG. 1.

From FIG. 2 it appears that two locking arms 5 are provided on the connector. In order to release the connector 3 the locking arms 5 must be pressed inwards while the connector 3 is retracted from the housing 1.

Figure 3:
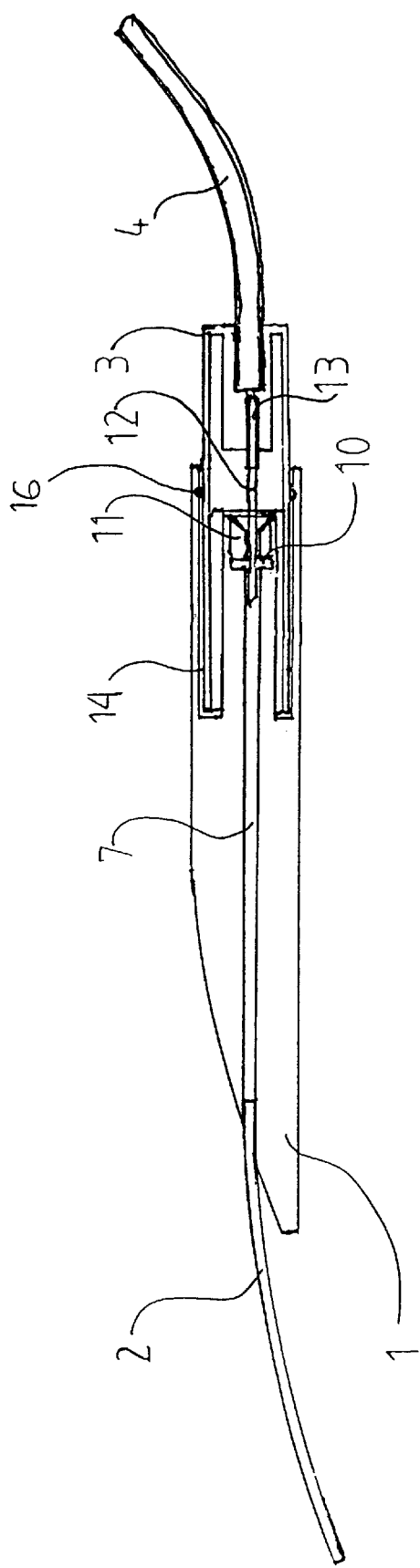
FIG. 3 is a cross section along the line 3—3 in FIG. 1.

From FIG. 3 it appears that the housing is provided with a bore 7, where at one end of this bore the soft cannula 2 is mounted in flow communication with the bore. At the end of the bore opposite the soft cannula 2 the bore has an increased diameter where a self-sealing septum 11 is mounted and held by means of an element 10. The connector 3 comprises a bore where the hose 4 is connected in fluid communication with this bore 13 at one end of this and where at the end of the bore opposite the hose a hollow needle 12 is provided in fluid communication with the bore 13. The needle is provided for penetrating the self-sealing septum in the housing 1. The self-sealing septum provides a fluid and air seal towards the surroundings when the needle of the connector is retracted from the septum and further provides a air and fluid seal around the needle when inserted through the septum.

From FIG. 4 the connector appears in a state released from the housing. It appears that the connector comprises flexible locking arms forming part of the cylindrical side wall, where each of the flexible locking arms is provided by two incisions in the connector wall parallel to the needle access. The locking arms comprises a protrusion 16 adapted to cooperate with a corresponding groove 19 in a cavity 8 of the housing. The locking arms being resilient means that the protrusions will be released form the groove upon applying a force on the arms and hereby pivoting these in a direction towards the center of the connector whereupon the connector can be released from the housing by applying an axial force on the connector.

Figure 5:
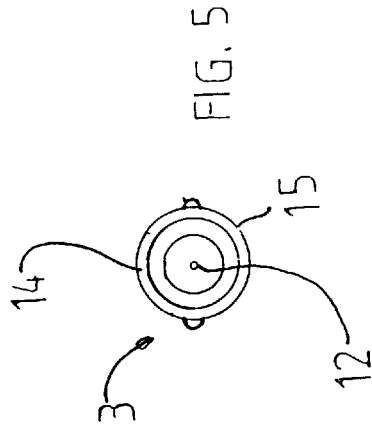
FIG. 5 is an end view of the connector shown in FIG. 4.

From FIG. 5 the front end of the connector 3 appears. The needle 12 and the circular guide means 14 are visualised. The connector having a circular cross section of the side wall 15 which extends beyond the needle means 12 that the connector can be guided and inserted into the housing at any angle in relation to the needle axis. Furthermore the fact that the guide means extend beyond the needle tip provides a protective shield against harmful injuries caused by the needle.

The circular, tubular guide means 14 is concentric with the needle 12, and the guide means 14 cooperates with a cavity 8 in the housing, as shown in FIG. 3. This cavity has a circular inner wall which mates with the side wall 15 of the guide means 14 such that the connector 3 is rotatable but not transversely dislocatable in the housing. In this embodiment the axis of the connector 3 is aligned with the needle 12, and the guide means 14 is arranged axis-symmetrically with respect to the axis of the connector.

What is claimed is:

1. A subcutaneous infusion device comprising:

a housing;

a flow channel within the housing;

a cannula extending from the housing and being in flow communication with the flow channel;

a connector for delivery of fluid into the flow channel;

guide means for guiding the connector into a delivery position, the guide means being arranged axis-symmetrically in relation to the axis of the connector; where the housing comprises a cavity, the cavity having a circular inner wall forming said guide means, and where the connector has an outer wall mating with the inner wall of the cavity in the housing in a rotatable but not transversely dislocatably manner upon insertion of the connector.

2. A subcutaneous infusion device as claimed in claim 1 where said housing and said connector respectively comprise cooperating interlocking means for interlocking the housing and the connector.

3. A subcutaneous infusion device as claimed in claim 2 where the interlocking means are arranged with an ability of interlocking in any angular position of the connector in relation to the housing.

4. A subcutaneous infusion device as claimed in claim 3 where the interlocking means form part of the outer wall of the connector mating with the inner wall of the cavity of the housing.

5. A subcutaneous infusion device as claimed in claim 4 where the connector comprises a hollow needle defining a needle axis, and where the outer wall of the connector is of a tubular configuration and comprises two incisions parallel to the needle axis, said two incisions providing a flexible locking arm serving as the interlocking means of the connector, the flexible locking arm having a protrusion, and where the inner wall of the cavity in the housing comprises a circumferential groove arranged to engage with the protrusion of the locking arm.

6. A subcutaneous infusion device as claimed in any of claims 1 and 2 to 5 where the outer wall of the connector mating with the inner wall of the cavity of the housing has an outer circular cross-section.

7. A subcutaneous infusion device comprising:

a housing;

a flow channel within the housing;

a cannula extending from the housing and being in flow communication with the flow channel;

a connector for delivery of fluid into the flow channel;

guide means for guiding the connector into a delivery position;

the guide means being arranged axis-symmetrically in relation to the axis of the connector; where the connector comprises a cavity, the cavity having a circular inner wall forming said guide means, and where the housing has an outer wall mating with the inner wall of the cavity in the connector in a rotatable but not transversely dislocatably manner upon mounting of the connector.

8. A subcutaneous infusion device as claimed in claim 7 where said housing and said connector respectively comprise cooperating interlocking means for interlocking the housing and the connector.

9. A subcutaneous infusion device as claimed in claim 8 where the interlocking means are arranged with an ability of interlocking in any angular position of the connector in relation to the housing.

10. A subcutaneous infusion device as claimed in any of claims 7, 8 and 9 where the outer wall of the housing mating with the inner wall of the cavity of the connector has an outer circular cross-section.

* * * * *